(12) United States Patent
Donahoe et al.

(10) Patent No.: US 11,207,196 B2
(45) Date of Patent: Dec. 28, 2021

(54) DEVICES AND METHODS FOR BONE FIXATION

(71) Applicant: NUVASIVE, INC., San Diego, CA (US)

(72) Inventors: Ryan Donahoe, San Diego, CA (US); Andrew Morris, San Diego, CA (US)

(73) Assignee: NUVASIVE, INC., San Diego, CA (US)

(*) Notice: Subject to any disclaimer, the term of this patent is extended or adjusted under 35 U.S.C. 154(b) by 0 days.

(21) Appl. No.: 16/725,031

(22) Filed: Dec. 23, 2019

(65) Prior Publication Data

US 2020/0129312 A1 Apr. 30, 2020

Related U.S. Application Data

(63) Continuation of application No. PCT/US2018/040463, filed on Jun. 29, 2018.
(Continued)

(51) Int. Cl.
| | |
|---|---|
| *A61F 2/46* | (2006.01) |
| *A61B 17/70* | (2006.01) |
| *A61B 17/80* | (2006.01) |
| *A61B 17/86* | (2006.01) |
| *A61F 2/44* | (2006.01) |

(Continued)

(52) U.S. Cl.
CPC ........ *A61F 2/4611* (2013.01); *A61B 17/7059* (2013.01); *A61B 17/8047* (2013.01); *A61B 17/86* (2013.01); *A61F 2/447* (2013.01); *A61B 2017/00955* (2013.01); *A61B 2017/564* (2013.01); *A61F 2002/30131* (2013.01); *A61F 2002/30593* (2013.01); *A61F 2002/30604* (2013.01); *A61F 2002/4683* (2013.01)

(58) Field of Classification Search
CPC . A61B 17/80; A61B 17/8033; A61B 17/8047; A61F 2/44; A61F 2/4455; A61F 2/446; A61F 2/4465; A61F 2/447; A61F 2/46; A61F 2/4611; A61F 2002/4683
See application file for complete search history.

(56) References Cited

U.S. PATENT DOCUMENTS

| | | | |
|---|---|---|---|
| 6,413,259 B1 | 7/2002 | Lyons et al. | |
| 6,605,090 B1 | 8/2003 | Trieu et al. | |

(Continued)

FOREIGN PATENT DOCUMENTS

CN 205697975 11/2016

OTHER PUBLICATIONS

International Search Report and Written Opinion for application serial No. PCT/US18/40463 dated Jan. 3, 2019.

*Primary Examiner* — Eric S Gibson
(74) *Attorney, Agent, or Firm* — Hoffman Warnick LLC

(57) ABSTRACT

Devices and methods for bone fixation including a bone fixation system including a bone plate or intervertebral spacer including a plurality of apertures dimensioned to receive bone fasteners and at least one polymeric element capable of transitioning from a solid state to a flowable state. The polymeric element transitions to a flowable state as a result of exposure to ultrasonic vibration. The polymeric element is placed on the bone plate or intervertebral spacer adjacent a fastener in an aperture and acts to prevent rotational and/or translational movement of the fastener relative to the bone plate or intervertebral spacer.

20 Claims, 5 Drawing Sheets

Related U.S. Application Data

(60) Provisional application No. 62/526,825, filed on Jun. 29, 2017.

(51) Int. Cl.
*A61B 17/00* (2006.01)
*A61B 17/56* (2006.01)
*A61F 2/30* (2006.01)

(56) References Cited

U.S. PATENT DOCUMENTS

| | | | |
|---|---|---|---|
| 7,335,205 B2* | 2/2008 | Aeschlimann | B29C 65/601 606/232 |
| 8,343,198 B2* | 1/2013 | Sommer | A61B 17/8605 606/291 |
| 9,220,609 B2* | 12/2015 | Mueller | A61F 2/447 |
| 2004/0030341 A1* | 2/2004 | Aeschlimann | B29C 66/727 606/232 |
| 2006/0155285 A1 | 7/2006 | Anderson et al. | |
| 2006/0276793 A1 | 7/2006 | Berry | |
| 2006/0276795 A1 | 12/2006 | Orbay et al. | |
| 2007/0265622 A1* | 11/2007 | Aeschlimann | A61B 17/84 606/60 |
| 2009/0198284 A1* | 8/2009 | Henry | A61B 17/8047 606/286 |
| 2010/0023057 A1* | 1/2010 | Aeschlimann | A61F 2/30749 606/246 |
| 2010/0114097 A1 | 5/2010 | Siravo et al. | |
| 2010/0179654 A1* | 7/2010 | Mayer | A61F 2/46 623/17.11 |
| 2010/0249850 A1* | 9/2010 | Cerynik | A61B 17/86 606/281 |
| 2010/0274358 A1* | 10/2010 | Mueller | A61B 17/7059 623/17.16 |
| 2011/0301713 A1 | 12/2011 | Theofilos | |
| 2012/0022535 A1* | 1/2012 | Mayer | A61B 17/68 606/75 |
| 2013/0110175 A1* | 5/2013 | Sommer | A61B 17/8605 606/281 |
| 2020/0129312 A1* | 4/2020 | Donahoe | A61F 2/4611 |
| 2020/0138495 A1* | 5/2020 | Mayer | A61B 17/7032 |
| 2020/0222089 A1* | 7/2020 | Mayer | A61B 17/8836 |
| 2020/0367948 A1* | 11/2020 | Mayer | A61B 17/8042 |

* cited by examiner

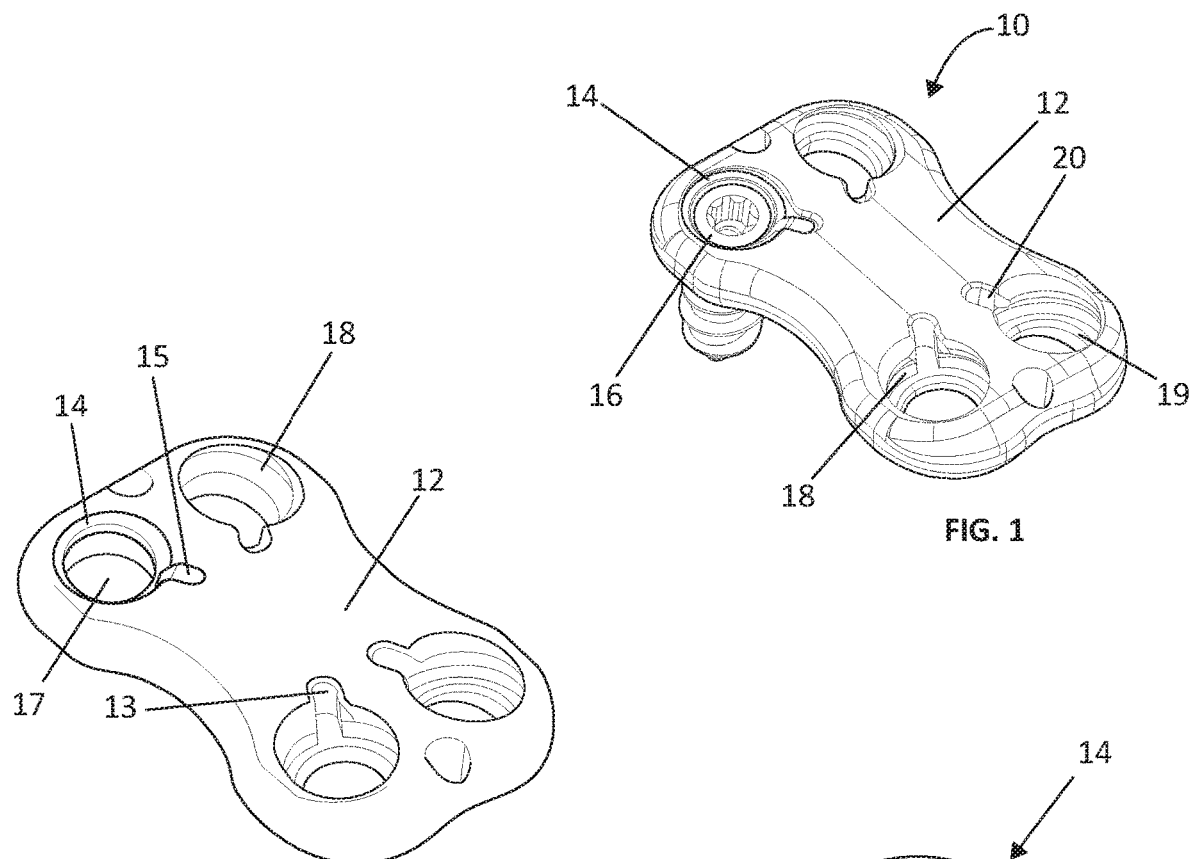
FIG. 1
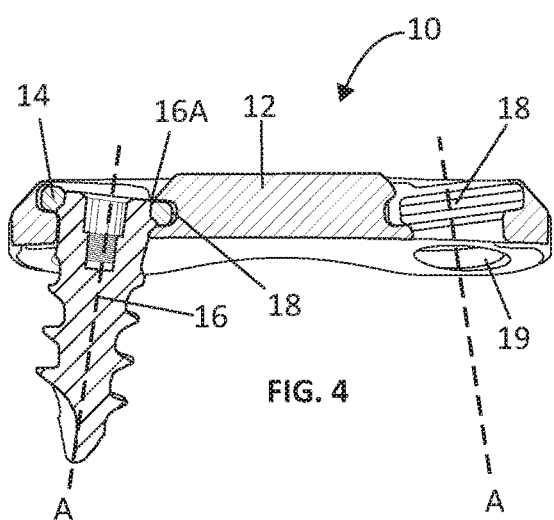
FIG. 2
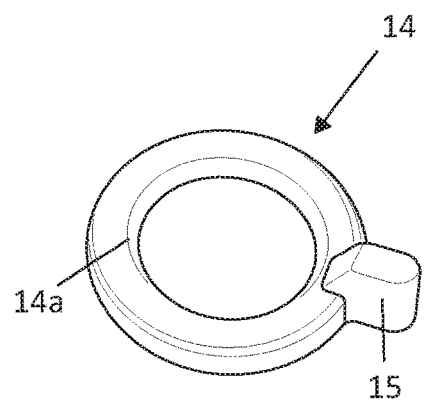
FIG. 3
FIG. 4

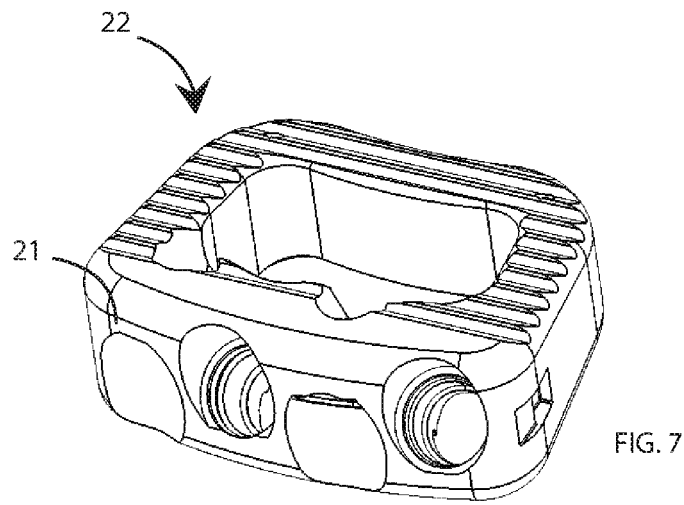
FIG. 7
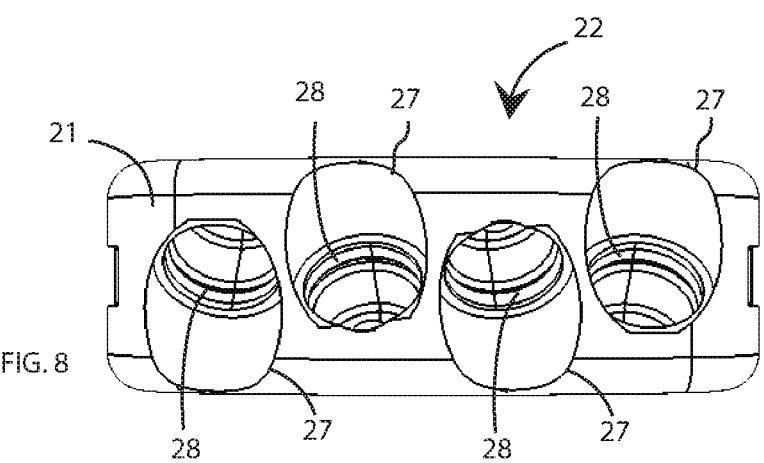
FIG. 8
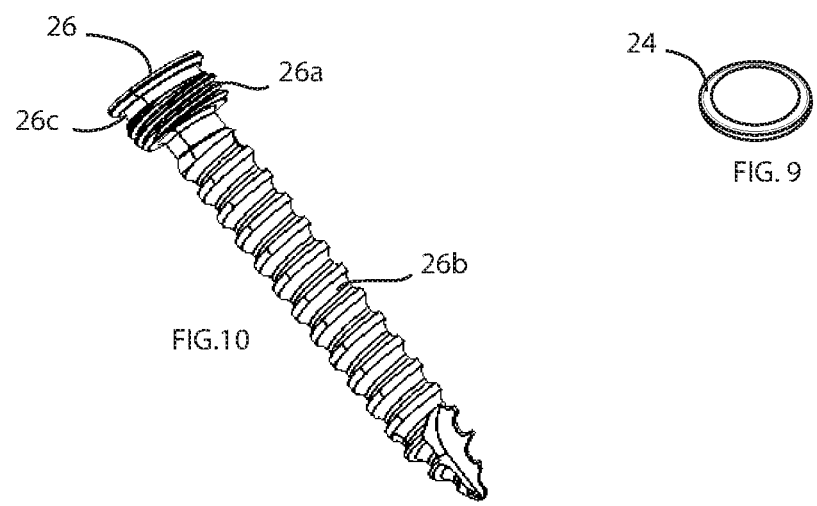
FIG. 10
FIG. 9

DEVICES AND METHODS FOR BONE FIXATION

CROSS REFERENCE TO RELATED APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

This invention relates generally to fastener anti-backout mechanisms for bone fixation devices.

Description of the Related Art

In the orthopedic medical device industry, bone screws are commonly used to secure various medical devices in position with respect to a patient's skeletal structure. Bone screw back-out, both rotational back-out and translational back-out, is a problem of particular concern in the medical device industry. As such, there is a need for improved anti-backout solutions for use with bone fixation devices.

Ultrasonic welding is an industrial technique whereby high-frequency ultrasonic acoustic vibrations are applied to workpieces being held together under pressure to create a solid-state weld. These high-frequency ultrasonic acoustic vibrations are generally provided by devices known to those skilled in the art as sonotrodes. Sonotrodes are commonly used in various arts to liquefy polymeric materials to ultrasonically weld materials together.

SUMMARY OF THE INVENTION

This disclosure concerns devices and methods for providing an anti-backout component to bone fixation devices comprising at least one bone fastener. Specifically, the disclosure is directed to in-situ ultrasonic welding solutions for bone fixations, to solve at least some of the problems existing in the prior art. The anti-backout component described below is contemplated for use in any application in orthopedic or spine surgery when movement of one or more components of an implant is desired at the time of implantation, and then prevention of movement of any of those same components relative to each other is desired after the implant has been implanted.

A first exemplary method for bone fixation is provided including the steps: positioning a plate adjacent to a patient's bone, the plate including an aperture dimensioned to receive a fastener there through and a polymeric element adjacent the aperture; inserting a fastener through the aperture; applying a sonotrode to the polymeric element until the polymeric element reaches a flowable state; allowing the polymeric element to flow into a space in the aperture that is adjacent the fastener, such that the polymeric element is in contact with both the plate and the fastener; allowing the polymeric element to harden to a solid state such that the polymeric element prevents the fastener from moving relative to the plate.

A second exemplary method for bone fixation, includes the steps of: positioning a spacer in an intervertebral disc space between a first vertebral body and a second vertebral body, the spacer including a wall having an aperture dimensioned for receiving a fastener therein and a polymeric element adjacent the aperture; inserting a fastener through the aperture and into one of the first and second vertebral bodies; applying a sonotrode to the polymeric element until the polymeric element reaches a flowable state; allowing the polymeric element to flow into a space adjacent the fastener in the aperture such that the polymeric element is in contact with both the wall of the spacer and the fastener; allowing the polymeric element to harden to a solid state, thereby preventing the fastener from moving relative to the wall of the spacer.

A first exemplary embodiment of a bone fixation system is provided, the bone fixation system including: a bone fixation having an aperture dimensioned to receive a fastener there through and a polymeric element adjacent the aperture; a fastener configured to secure the implant to a patient's bone; and a sonotrode.

A second embodiment of a bone fixation system is provided, the bone fixation system including: a spacer configured for placement within an intervertebral disc space of a patient between a first vertebral body and a second vertebral body, the spacer further including: a wall having at least one aperture dimensioned for receiving a fastener there through and at least one polymeric element disposed adjacent to each aperture; at least one fastener configured to extend through one of the one or more apertures to secure the spacer to one of the first and second vertebral bodies; a sonotrode configured change a physical state of the polymeric element; wherein upon introducing the sonotrode to the polymeric element, material of the polymeric element flows into a space adjacent the fastener in the aperture such that the material of the polymeric element is in contact with both the wall of the spacer and the fastener; and wherein upon removing the sonotrode from the polymeric element, the material of the polymeric element is configured to harden to a solid state, thereby preventing the fastener from moving relative to the wall of the spacer. A first embodiment of a method for bone fixation, includes the steps of: positioning a plate adjacent to a patient's bone, the plate including an aperture dimensioned to receive a fastener there through and a polymeric element adjacent the aperture; inserting a fastener through the aperture; applying a sonotrode to the polymeric element until the polymeric element reaches a flowable state; allowing the polymeric element to flow into a space in the aperture that is adjacent the fastener, such that the polymeric element is in contact with both the plate and the fastener; allowing the polymeric element to harden to a solid state such that the polymeric element prevents the fastener from moving relative to the plate.

In some embodiments, the plate includes a recess in a surface of the plate, wherein the recess is in communication with at least a portion of the at least one aperture.

In some embodiments, the polymeric element may be installed in the recess prior to positioning the plate adjacent to a patient's bone, or subsequent to positioning the plate adjacent to the patient's bone.

In some embodiments, the plate comes preassembled with the polymeric element installed in the recess.

In some embodiments, the recess may be in communication with the at least one aperture along at least a portion of the perimeter of the aperture. In some embodiments the recess may be in communication with the at least one aperture along the entire perimeter of the aperture.

In some embodiments, the polymeric element may be made out of a thermoplastic material. The thermoplastic material may liquefy when in contact with a sonotrode. Once liquefied the polymeric material may flow for e.g. into the recess on the circumferential surface of the head of the fastener.

In some embodiments, the polymeric element and/or material may prevent the fastener from translating in a direction opposite of the direction of insertion. In some embodiments the polymeric element and/or material may prevent the fastener from rotating.

In some embodiments, the fastener may include a shank portion and a head portion having a circumferential surface, wherein the circumferential surface of the head comprises a recess. After the fastener is inserted through the plate, and a sonotrode is introduced to liquefy the polymeric element, the polymeric element may flow into the recess of the head of the fastener, to help secure the fastener with respect to the plate.

In some embodiments, the plate may be configured for fixation on any region of a patient's skeletal system including for example: spinal fixation or long bone fixation.

The plate may include one or more apertures, each aperture dimensioned to receive a fastener there through. One or more fasteners may be inserted through each of the respective apertures. The plate may include a recess in a surface of the plate that is adjacent to and in communication with at one or more apertures. The recess in the surface of the plate may be adjacent to and in communication with each of a plurality of apertures.

In some embodiments, the plate may include a recess in a surface of the plate that is adjacent to and in communication with at least two apertures. In such embodiments, the polymeric material to may be allowed to flow in the at least two apertures.

In some embodiments, the recess in the surface of the plate may be adjacent to and in communication with each of a plurality of apertures. In such embodiments, the polymeric material may be allowed to flow in each of the plurality of apertures.

A second embodiment of a method for bone fixation is provided, including the steps of: positioning a spacer in an intervertebral disc space between a first vertebral body and a second vertebral body, the spacer including a wall having an aperture dimensioned for receiving a fastener there through, and a polymeric element adjacent the aperture; inserting a fastener through the aperture and into one of the first and second vertebral bodies; applying a sonotrode to the polymeric element until the polymeric element reaches a flowable state; allowing the polymeric element to flow into a space adjacent the fastener in the aperture such that the polymeric element is in contact with both the wall of the spacer and the fastener; allowing the polymeric element to harden to a solid state, thereby preventing the fastener from moving relative to the wall of the spacer.

In some embodiments, the spacer is a unitary piece. In some embodiments, the spacer may include a modular spacer with a body that is detachable from a wall. The body may inserted into the intervertebral disc space separately from the wall.

In some embodiments, the body may be generally U-shaped. The wall may composed of a material different than the body of the spacer. One or more of the wall and the body may include one or more apertures, each aperture dimensioned to receive a fastener therein. One or more of the wall and the body may include a recess in a surface of the wall, wherein the recess is in communication with the aperture.

In some embodiments, the step of inserting a fastener through the aperture may include inserting a plurality of fasteners through respective apertures.

In some embodiments, the polymeric element may be installed in the recess prior to the step of positioning the spacer into the intervertebral disc space. The polymeric element may be made from a thermoplastic material. The polymeric element may prevent the fastener from translating in a direction opposite of the direction of insertion. The polymeric element may also prevent the fastener from rotating.

In some embodiment, the recess may be in communication with the at least one aperture along at least a portion of the perimeter of the aperture. The recess may be in communication with the at least one aperture along the entire perimeter of the aperture.

In some embodiments, the fastener may include a shank portion and a head portion having a circumferential surface, wherein the circumferential surface of the head comprises a recess.

In some embodiments, after applying a sonotrode to the polymeric element until the polymeric element reaches a flowable state the polymeric material may be allowed to flow into the recess on the circumferential surface of the head of the fastener while in the flowable state.

In some embodiments, the wall may include a recess in a surface of the wall that is adjacent to and in communication with at least two apertures.

A first embodiment of a bone fixation system is provided, the bone fixation system including: a bone fixation having an aperture dimensioned to receive a fastener there through and a polymeric element adjacent the aperture; a fastener configured to secure the implant to a patient's bone; and a sonotrode.

In some embodiments, the bone fixation may be for e.g. a fixation plate, a spacer, an expandable spacer, a distraction rod, an intramedullary nail, or any other bone fixation. In some embodiments, the bone fixation may be configured for spinal fixation, in other embodiments the bone fixation may be configured long bone fixation. As one with skill in the art may appreciate, the implant may be configured for use in any medical procedure requiring an implant.

In some embodiments, the bone fixation may include a plurality of apertures dimensioned to receive a fastener there through. The system may further include a plurality of fasteners.

In some embodiments the implant may be a fixation plate having a recess in a surface of the plate, wherein the recess is in communication with the aperture. The polymeric element may be installed in the recess prior to the step of positioning the fixation plate adjacent to a patient's bone.

In some embodiments, the recess may be in communication with the at least one aperture along at least a portion of the perimeter of the aperture. The recess may be in communication with the at least one aperture along the entire perimeter of the aperture.

In some embodiments the polymeric element is made out of a thermoplastic material. The polymeric element may prevent the fastener from translating in a direction opposite of the direction of insertion. In some embodiments the polymeric element may prevent the fastener from rotating.

In some embodiments, the fastener may include a shank portion and a head portion having a circumferential surface, wherein the circumferential surface of the head comprises a recess. The polymeric material may be allowed to flow into the recess on the circumferential surface of the head of the fastener while in a flowable state.

In some embodiments where the bone fixation is an intervertebral spacer, the spacer may be a single, unitary piece. In some embodiments an aperture may be located on a wall of the spacer. The wall may be an anterior wall of the intervertebral spacer. The wall may be detachable from the body of the intervertebral spacer. The body may be generally U-shaped.

A second embodiment of a bone fixation system is provided, the bone fixation system including: a spacer configured for placement within an intervertebral disc space of a patient between a first vertebral body and a second vertebral body, the spacer further including: a wall having at least one aperture dimensioned for receiving a fastener there through and at least one polymeric element disposed adjacent to each aperture; at least one fastener configured to extend through one of the one or more apertures to secure the spacer to one of the first and second vertebral bodies; a sonotrode configured change a physical state of the polymeric element; wherein upon introducing the sonotrode to the polymeric element, material of the polymeric element flows into a space adjacent the fastener in the aperture such that the material of the polymeric element is in contact with both the wall of the spacer and the fastener; and wherein upon removing the sonotrode from the polymeric element, the material of the polymeric element is configured to harden to a solid state, thereby preventing the fastener from moving relative to the wall of the spacer.

In some embodiments, the spacer may be a unitary piece. The spacer may have a body that is detachable from the wall. The body may be configured to be inserted into the intervertebral disc space separately from the wall. The body may be generally U-shaped. The wall may be made out of a different material than the body of the spacer. The wall may have a plurality of apertures, each dimensioned to receive a fastener therein.

The bone fixation system may include a plurality of fasteners configured to extend through a respective plurality of apertures.

In some embodiments, the polymeric element may be installed in the recess prior to the positioning the spacer into the intervertebral disc space. The polymeric element may be made out of a thermoplastic material. The polymeric element may prevent the fastener from translating in a direction opposite of the direction of insertion. The polymeric element may also prevent the fastener from rotating.

The fasteners may include a shank portion and a head portion having a circumferential surface, wherein the circumferential surface of the head comprises a recess. The polymeric material may be allowed to flow into the recess on the circumferential surface of the head of the fastener while in the flowable state.

In some embodiments the wall may a recess in a surface of the wall that is adjacent to and in communication with at least two apertures. The polymeric material may be allowed to flow into the at least two apertures. The recess may be in the surface of the wall adjacent to and in communication with each of the plurality of apertures.

These and other features and benefits are further described in the following detailed description.

BRIEF DESCRIPTION OF THE DRAWINGS

FIG. 1 shows a perspective view of a bone fixation system in accordance with a first embodiment;

FIG. 2 shows a perspective view of the bone fixation system of FIG. 1;

FIG. 3 shows a perspective view of a polymeric element of the bone fixation system of FIG. 1;

FIG. 4 shows a cross-sectional side view of the bone fixation system of FIG. 1;

FIG. 7 shows a perspective view of the interbody spacer component of the bone fixation system of FIG. 5;

FIG. 8 shows a front view of the intervertebral spacer of the bone fixation system of FIG. 5;

FIG. 9 shows a polymeric element in accordance with a second embodiment;

FIG. 10 shows an embodiment of a fastener of the bone fixation system of FIG. 5;

DETAILED DESCRIPTION OF THE PREFERRED EMBODIMENTS

Figure 5:
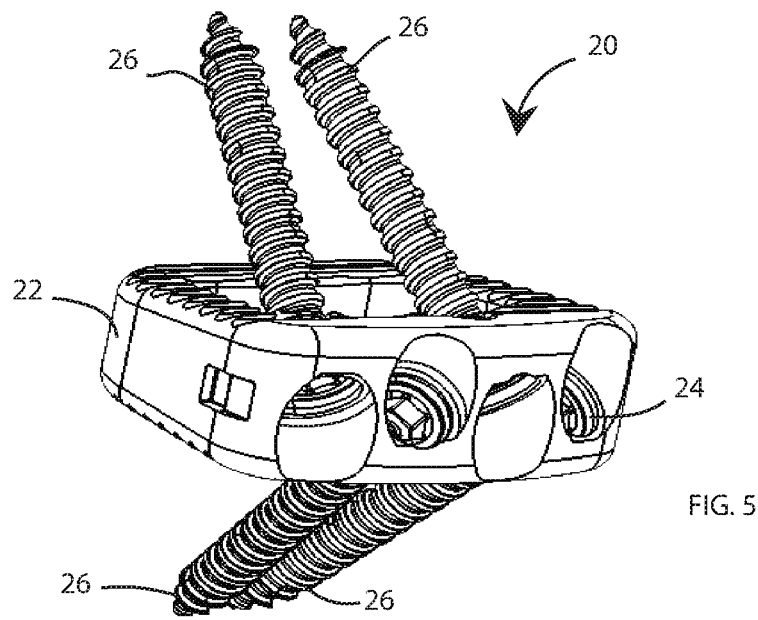
FIG. 5 shows perspective view of a bone fixation implant system in accordance with a second embodiment.
Figure 6:
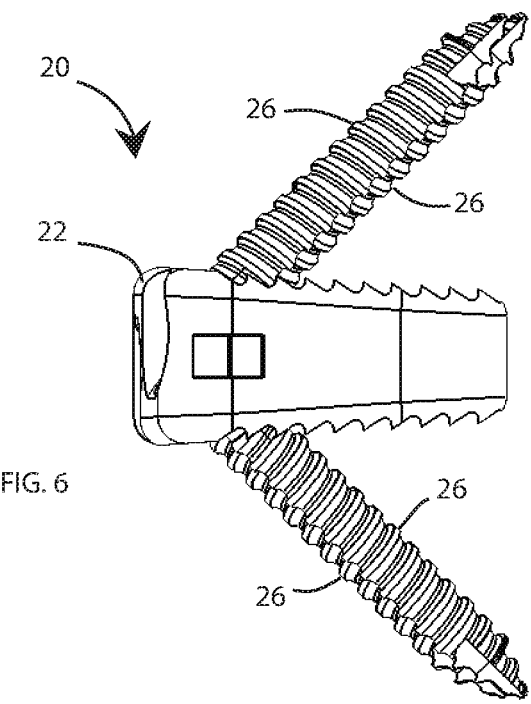
FIG. 6 shows side view of the bone fixation system of FIG. 5.

For purposes of explanation and not limitation, details and descriptions of certain preferred embodiments are hereinafter provided such that one having ordinary skill in the art may be enabled to make and use the invention. These details and descriptions are representative only of certain preferred embodiments, however a myriad of other embodiments which will not be expressly described will be readily understood by those having skill in the art upon a thorough review hereof. Accordingly, any reviewer of the instant disclosure should interpret the scope of the invention by the claims, and such scope shall not be limited by the embodiments described and illustrated herein.

As one with skill in the art may appreciate, the bone fixation system 10 may include any device intended to be placed adjacent a bone within the human body including: plates and interbody spacers. The bone fixation system may be constructed out of any suitable biocompatible materials including, for example, autograft, allograft, titanium, cobalt chrome, carbon fiber, PEEK, PEK, PEKK or a combination thereof, or any other material known in the field of bone fixation technology.

FIGS. 1-4 illustrate an exemplary embodiment of a bone fixation system including a bone plate 12, a plurality of fasteners 16 and a polymeric element 14. According this exemplary embodiment, the bone plate 12 includes a plurality of apertures 17 each dimensioned to receive a fastener 16 there through. The bone plate 12 further includes a recess 18 adjacent each aperture 17, the recess 18 being configured to house the polymeric element 14. As shown in this embodiment, each recess 18 corresponds to a single aperture 17. However, plate configurations are also contemplated wherein a single recess is in communication with two, three, four or more apertures.

According to one aspect, the fastener 16 may include any device intended to secure an implant with respect to a bone structure of a patient. By way of example only a fastener may include, but is not limited to, a bone anchor, a bone screw, a spike, a staple or a blade. As illustrated in the exemplary embodiment in FIG. 4, the fastener 16 is a bone screw that includes a head and a threaded shank.

According to another aspect, the polymeric element is at least partially comprised of a thermoplastic material. According to the exemplary embodiment, the thermoplastic material that can transition from a generally solid state (e.g. not flowable) flowable state when the thermoplastic material is heated. In particular, the thermoplastic material transitions from a solid state at room temperature to a flowable state upon application of ultrasonic vibration to the polymeric element. According to the exemplary embodiment, the bone fixation system 10 pre-assembled prior to use in surgery such that the polymeric element 14 is housed within the recess 18 of the plate 12. The polymeric element 14 may be dimensioned to correspond to the shape of the recess 17 in the bone plate 12 to which the polymeric element 14 is applied. According to this embodiment, the polymeric element 14 has an annular shape that corresponds generally to the shape of the aperture 17 and has an inner diameter 14a that is dimensioned to allow passage of the fastener through the center of the polymeric element. FIG. 3 shows a perspective view of a polymeric element 14 having an inner diameter 14a dimensioned to receive a fastener 16. The size of the inner diameter 14a may be chosen depending on the type and size of fastener 16 used. However, preassembly of the plate 12 and polymeric element 14 is not required, and the polymeric element(s) 14 may be provided separately to be assembled, for example, during surgery.

In some embodiments, a keyed portion 13 or any portion of the polymeric element 14, remain accessible even with a fastener 16 inserted through a corresponding aperture 17. This accessible portion 24 of the polymeric element is sized to allow sufficient contact with the distal tip 45 of a sonotrode 40, in order to apply ultrasonic vibrations to the polymeric element thereby causing the thermoplastic component(s) to become heated and consequently transition to a flowable state.

In some embodiments, the plate 12 may include a corresponding anti-rotation groove 13, (see FIG. 2) such that when the polymeric element 14 is placed adjacent to the aperture 17, the anti-rotation feature 15 of the polymeric element 14 will complementarily fit within the anti-rotation feature 13 of the plate 12. This interaction may prevent the polymeric element 14 from rotating when a fastener 16 is inserted through the apertures 17.

During use, a bone plate is implanted adjacent a patient's bone. According to the exemplary embodiment, the polymeric element is pre-installed in the recess in the bone plate prior to implantation in a patient. Upon placement of the bone plate adjacent the patient's bone, at least one fastener is inserted through an aperture and into the patient's bone to secure the bone plate to the bone. After placement of the one or more fasteners, the plate may be secured with respect to the bone of a patient, and the surgeon can ultrasonically weld the fasteners to the plate. In doing so, the surgeon may for example, introduce the distal tip of a sonotrode to the thermoplastic element. Application of ultrasonic vibration from the sonotrode to the polymeric element causes the thermoplastic component(s) to heat up and consequently become flowable. The flowable thermoplastic material is then allowed to flow into the aperture and infiltrate the space in and/or around the proximal end of the fastener within the aperture. The polymeric element is then allowed to cool and return to a solid state, thereby preventing the fastener from rotating and/or translating in the aperture of the plate. According to one aspect, once the polymeric element has infiltrated the space in and/or around the proximal end of the fastener, it is actively cooled to a solid state. According to another aspect, thermoplastic material may flow into grooves on the fastener, or over the heads of the fasteners. Additionally, thermoplastic material may flow within the keyed groove of the plate. In an alternative method, the polymeric element is provided separately from the bone plate, and is applied to the bone plate after the steps of applying the bone plate to the patient's bone and inserting the fasteners through the apertures in the bone plate.

FIG. 4 shows a cross-sectional side view of a bone fixation system 10 in accordance with the first embodiment, the bone fixation system 10 shown including at least one fastener 16 inserted there through, with a portion of a polymeric element 14 disposed between the fastener 16 and the plate 12. The polymeric element 14 is shown securing the bone fixation device 16 relative to the plate 12.

FIGS. 5-10 illustrate an alternative exemplary embodiment, having many of the same features as the embodiment described above and shown in FIGS. 1-4. FIG. 5 shows perspective view of a bone fixation system 20 in accordance with a second embodiment, the bone fixation system 20 shown including an intervertebral spacer 22 having a wall 21 that includes at least one aperture 27 there through. According to the exemplary embodiment shown in FIG. 5, the spacer 22 has an anterior wall 21 with a plurality of apertures 27 dimensioned to receive bone fasteners 36. Each of the apertures 27 has a corresponding recess 28 dimensioned to house the polymeric element 24. It is also contemplated that wall 21 of the spacer 22 can include fewer recesses than apertures, wherein a single recess is in communication with more than one aperture.

According to this exemplary embodiment, FIG. 7 shows a perspective view of the spacer having a one or more apertures disposed on an anterior wall 21 thereof. The spacer 22 is shown having a top surface, a bottom surface, and one or more walls forming a fusion aperture. The top surface is shown including anti-migration features to engage the endplates of the vertebral bodies adjacent the intervertebral space into which the spacer is inserted. The fusion aperture is configured to receive bone graft, or bone graft substitute material therein, to promote fusion across the disc space.

In some embodiments, the polymeric element 24 may come preinstalled adjacent to the aperture 27 of the spacer 22. In other embodiments, the polymeric element may come preinstalled adjacent to the fastener 26. In still some other embodiments, the polymeric element 24 may be provided separately from the intervertebral spacer and positioned as need to secure to secure the fastener(s) 26 with respect to the spacer 22 during surgery.

In some embodiments, at least a portion of the polymeric element 24 remains exposed after a fastener 26 is inserted through an aperture 27 of the spacer 22. As described in the previous embodiment, the distal tip of a sonotrode is applied to the exposed portion of the polymeric element to transmit ultrasonic vibrations to the polymeric element, causing it to heat up and transition to a flowable state. Additionally, an exposed portion of the polymeric element 24 may be achieved for e.g.: by creating a channel in the spacer 22, creating a channel in the fastener 26, or including an anti-rotation feature on the polymeric element 24, similar to the anti-rotation feature of the first embodiment.

During use, the bone fixation device according to the embodiment illustrated in FIGS. 5-10 is installed in a similar method. Specifically, the polymeric element(s) are pre-installed in recesses in the aperture(s) of the spacer and the spacer is introduced into the intervertebral space of a patient. Upon desired placement of the spacer, at least one fastener is inserted into an aperture in the spacer. After insertion of the fastener, the distal tip of a sonotrode is applied to the polymeric element to transmit ultrasonic vibrations to the polymeric element, causing the polymeric element to heat up and transition to a flowable state. The flowable polymeric element is allowed to flow into the space in the aperture adjacent to the proximal end of the fastener, and allowed to cool to a solid state. Once in a solid state, the polymeric element prevents rotation and/or translation of the fastener with respect to the spacer. According to an alternative method, the polymeric element is provided separately from the spacer, and is applied to the aperture of the spacer after the fastener has been inserted.

Figure 11:
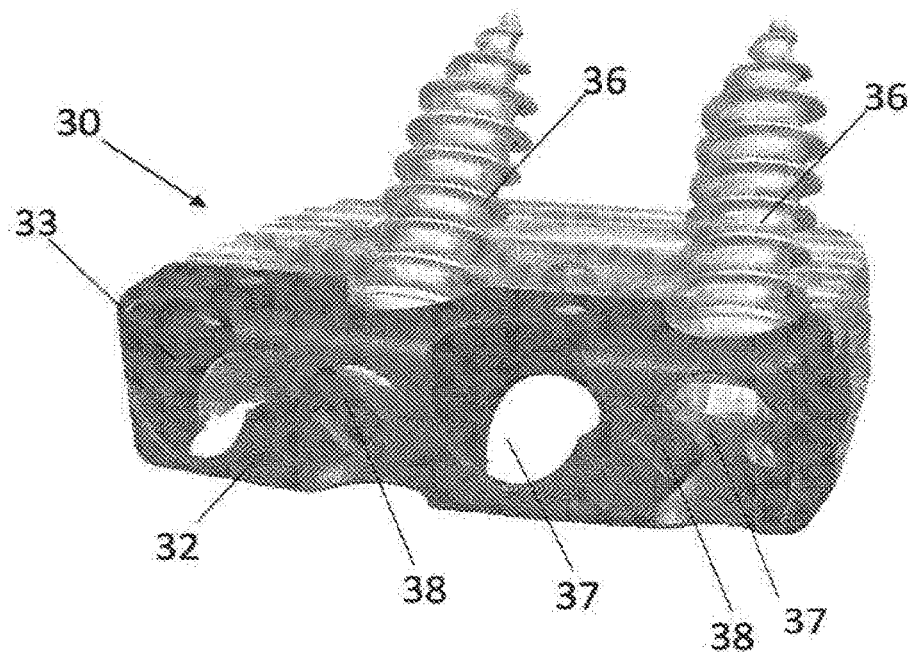
FIG. 11 shows a perspective view of a bone fixation system in accordance with a third embodiment.
Figure 12:
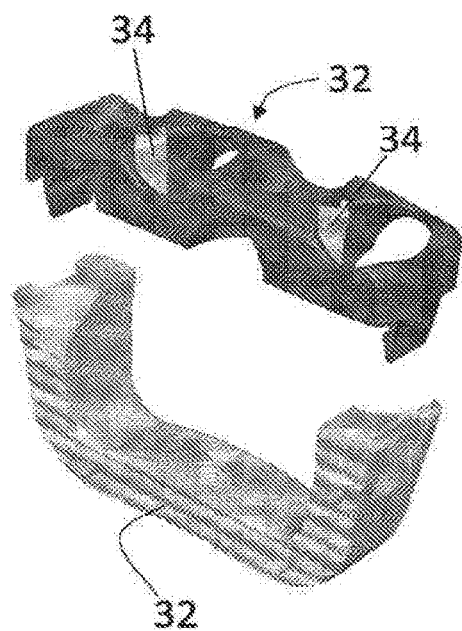
FIG. 12 shows an exploded perspective view of the bone fixation system of FIG. 11.
Figure 13:
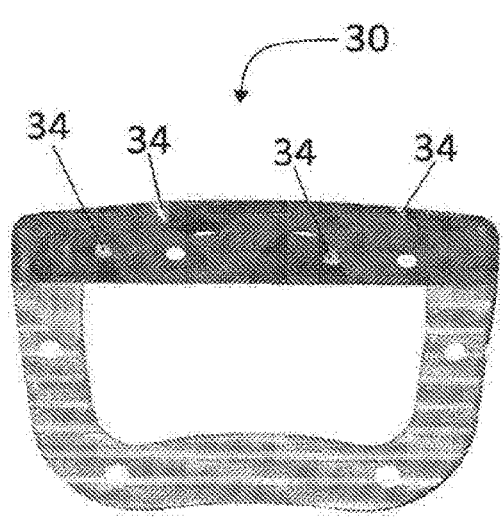
FIG. 13 shows a view top of the bone fixation system of FIG. 11.

FIGS. 11-13 illustrate a bone fixation system 30 in accordance with a third embodiment, the bone fixation system 30 is used in the same way and includes substantially the same features as shown in the exemplary embodiment of FIGS. 5-10, but further including a modular intervertebral spacer including a body 32, and a detachable wall 33, the detachable wall 33 including a plurality of apertures dimensioned to receive a plurality of fasteners 37 configured to secure the modular intervertebral spacer in an intervertebral space of a patient The detachable wall 33 includes a plurality of recesses 38, each recess 38 adjacent to and in communication with two apertures 37. Each recess 38 is configured to house a polymeric element 34 therein.

In some embodiments, the modular intervertebral spacer system 32, 33 may include any spacer system having two or more parts, wherein two or more of the parts are joined together to form a unitary spacer body. In use, the modular intervertebral spacer may be pre-assembled prior to insertion, or the body 32 and the detachable wall 33 may be inserted separately. The body and detachable may be comprised of the same material or different materials. By way of example only, the body 32 may be constructed of a plastic material and the detachable wall 33 may be constructed of titanium or other suitable medical grade metal, or vice versa.

Figure 14:
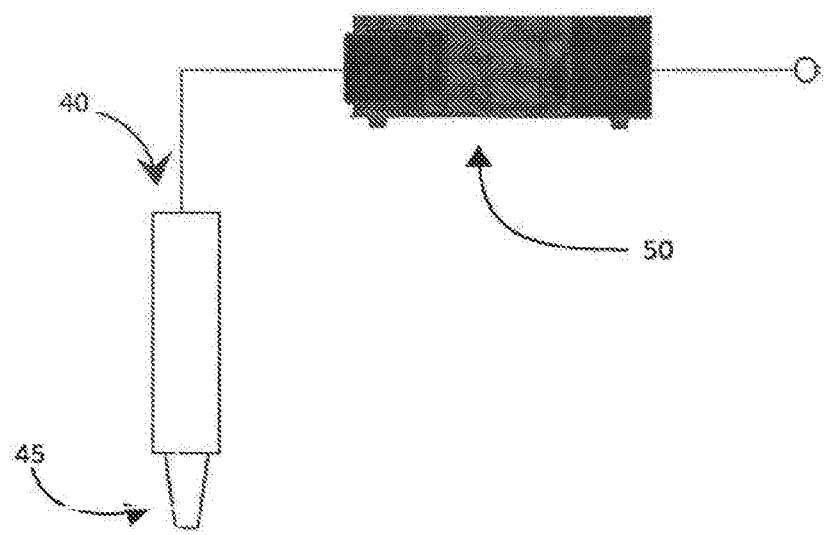
FIG. 14 shows a diagram of an exemplary sonotrode system.

FIG. 14 shows a diagram of an exemplary sonotrode 40 configured to apply ultrasonic vibrations to cause the polymeric element to transition from a solid state to a flowable state. The ultrasonic vibrations may be created by a series of components, for example: a power supply, a converter, a booster, and a horn.

The power supply may receive an electrical line voltage and convert it to an operating frequency (e.g. 20 kHz). This electrical energy may be sent through a radio-frequency cable to a converter. The converter may use piezoelectric ceramics to convert the electrical energy to mechanical vibrations at an operating frequency of the power supply. This mechanical vibration may be increased or decreased depending on the configuration of the booster and horn. Depending on the polymeric materials used in the parts.

In operation, mechanical vibrations may be delivered to the parts to be welded. The parts also may be put under a mechanical load. Under this load, the mechanical vibrations may be transmitted to the interface between the material surfaces, which focuses the vibration to create intermolecular and surface friction. This friction creates heat and a subsequent transition from solid to liquid. The solid may then solidify into a welded bond.

Now, although particular features and embodiments have been described in an effort to enable those with skill in the art to make and use the claimed invention, it should be understood that several variations, alterations or substitutions can be achieved to arrive at a container with integrated dome applicator and hinged cap. Nothing in this description shall be construed as limiting the spirit and scope of the invention as set forth in the appended claims, below.

What is claimed is:

1. A method for bone fixation, comprising the steps of:
positioning a spacer in an intervertebral disc space between a first vertebral body and a second vertebral body, the spacer including a wall having an aperture dimensioned for receiving a fastener there through and a polymeric element adjacent the aperture;
inserting a fastener through the aperture and into one of the first and second vertebral bodies;
applying a sonotrode to the polymeric element until the polymeric element reaches a flowable state;
allowing the polymeric element to flow into a space adjacent the fastener in the aperture such that the polymeric element is in contact with both the wall of the spacer and the fastener;
allowing the polymeric element to harden to a solid state, thereby preventing the fastener from moving relative to the wall of the spacer.

2. The method of claim 1, wherein the spacer is a unitary piece.

3. The method of claim 1, wherein the spacer includes a body that is detachable from the wall.

4. The method of claim 3, wherein the body is inserted into the intervertebral disc space separately from the wall.

5. The method of claim 3, wherein the body is generally U-shaped.

6. The method of claim 3, wherein the wall comprises a different material than the body of the spacer.

7. The method of claim 1, wherein the wall includes a plurality of apertures, each dimensioned to receive a fastener therein.

8. The method of claim 7, wherein the step of inserting the fastener through the aperture includes inserting a plurality of fasteners through respective apertures.

9. The method of claim 7, wherein the wall includes a recess in a surface of the wall that is adjacent to and in communication with at least two of the plurality of apertures.

10. The method of claim 9, further comprising allowing the polymeric material to flow in the at least two apertures.

11. The method of claim 7, wherein a recess in a surface of the wall is adjacent to and in communication with each of the plurality of apertures.

12. The method of claim 11, further comprising allowing the polymeric material to flow in each of the plurality of apertures.

13. The method of claim 1, wherein the wall includes a recess in a surface of the wall, wherein the recess is in communication with the aperture.

14. The method of claim 13, wherein the polymeric element is installed in the recess prior to the step of positioning the spacer into the intervertebral disc space.

15. The method of claim 13, wherein the recess is in communication with the aperture along at least a portion of a perimeter of the aperture.

16. The method of claim 15, wherein the recess is in communication with the aperture along an entirety of the perimeter of the aperture.

17. The method of claim 1, wherein the polymeric element comprises a thermoplastic material.

18. The method of claim 1, wherein the polymeric element prevents the fastener from translating in a direction opposite of a direction of insertion of the fastener.

19. The method of claim 1, wherein the polymeric element prevents the fastener from rotating.

20. The method of claim 1, wherein the fastener comprises:
- a shank portion and a head portion having a circumferential surface,
- wherein the circumferential surface of the head comprises a recess, and
- wherein the polymeric material is allowed to flow into the recess on the circumferential surface of the head of the fastener while in the flowable state.

\* \* \* \* \*